(12) United States Patent
Iyengar et al.

(10) Patent No.: US 10,835,181 B2
(45) Date of Patent: Nov. 17, 2020

(54) APPARATUSES, METHODS, AND SYSTEMS FOR MEASURING INSOLE DEFORMATION

(71) Applicant: Fossil Group, Inc., Richardson, TX (US)

(72) Inventors: Sridhar Iyengar, Salem, NH (US); Matthew Charles Diamond, San Francisco, CA (US)

(73) Assignee: Fossil Group, Inc., Richardson, TX (US)

( * ) Notice: Subject to any disclaimer, the term of this patent is extended or adjusted under 35 U.S.C. 154(b) by 314 days.

(21) Appl. No.: 15/184,047

(22) Filed: Jun. 16, 2016

(65) Prior Publication Data

US 2016/0367192 A1 Dec. 22, 2016

Related U.S. Application Data

(60) Provisional application No. 62/180,428, filed on Jun. 16, 2015.

(51) Int. Cl.
*A61B 5/00* (2006.01)
*A43B 17/03* (2006.01)
(Continued)

(52) U.S. Cl.
CPC .......... *A61B 5/6807* (2013.01); *A43B 3/0005* (2013.01); *A43B 17/026* (2013.01); *A43B 17/035* (2013.01); *A61B 5/1038* (2013.01); *A61B 2560/0475* (2013.01); *A61B 2562/0247* (2013.01); *A61B 2562/0266* (2013.01); *A61B 2562/0271* (2013.01); *A61B 2562/168* (2013.01)

(58) Field of Classification Search
CPC .... A43B 3/0005; A43B 13/203; A61B 5/1036
See application file for complete search history.

(56) References Cited

U.S. PATENT DOCUMENTS 5,642,096 A 6/1997 Leyerer et al.
5,753,061 A 5/1998 Rudy
(Continued)

FOREIGN PATENT DOCUMENTS

WO WO 2004/008095 A2 2/2004

OTHER PUBLICATIONS

International Search Report and Written Opinion dated Jun. 24, 2016 from International Application No. PCT/US2016/024144.
(Continued)

*Primary Examiner* — Patrick Fernandes
(74) *Attorney, Agent, or Firm* — Cooley LLP

(57) ABSTRACT

Devices, systems, and, methods for measuring deformation variation in an insole to determine characteristics of a user, including weight and gait, are described herein. In some embodiments, a device includes an insole having a fluid reservoir configured to be disposed in a shoe, a deformation sensor, and a communications module. The fluid reservoir includes a first portion and a second portion. The deformation sensor is coupled to the fluid reservoir and is configured to measure a deformation in at least one of the first portion and the second portion. The communications module is configured to receive the measured deformation from the deformation sensor and transmit the measured deformation to a remote device.

26 Claims, 10 Drawing Sheets

(51) Int. Cl.
*A43B 17/02* (2006.01)
*A43B 3/00* (2006.01)
*A61B 5/103* (2006.01)

(56) References Cited

U.S. PATENT DOCUMENTS

| | | |
|---|---|---|
| 5,875,571 A | 3/1999 | Huang |
| 5,915,819 A | 6/1999 | Gooding |
| 6,174,294 B1 | 1/2001 | Crabb et al. |
| 7,998,092 B2* | 8/2011 | Avni .................... A61B 5/1036 600/587 |
| 8,280,682 B2 | 10/2012 | Vock et al. |
| 8,384,551 B2 | 2/2013 | Ross et al. |
| 9,066,558 B2 | 6/2015 | Molyneux et al. |
| 2003/0009913 A1 | 1/2003 | Potter et al. |
| 2003/0163287 A1* | 8/2003 | Vock .................... A43B 3/0005 702/187 |
| 2003/0217484 A1* | 11/2003 | Christensen ........... A43B 13/20 36/29 |
| 2005/0132617 A1 | 6/2005 | Potter et al. |
| 2005/0261609 A1 | 11/2005 | Collings et al. |
| 2006/0162464 A1* | 7/2006 | Hayashi .................. A61B 5/16 73/818 |
| 2006/0248750 A1 | 11/2006 | Rosenberg |
| 2006/0282017 A1* | 12/2006 | Avni .................... A61B 5/1036 600/587 |
| 2008/0167580 A1 | 7/2008 | Avni et al. |
| 2010/0305478 A1 | 12/2010 | Ordway et al. |
| 2011/0214501 A1* | 9/2011 | Ross .................... A43B 3/0005 73/172 |
| 2011/0301504 A1 | 12/2011 | Lan et al. |
| 2013/0219745 A1 | 8/2013 | Moreno-Collado |
| 2014/0131120 A1 | 5/2014 | Horst et al. |
| 2014/0165427 A1* | 6/2014 | Molyneux ........... A43B 13/203 36/102 |
| 2016/0331322 A1 | 11/2016 | Son et al. |

OTHER PUBLICATIONS

International Search Report and Written Opinion dated Sep. 7, 2016 from International Application No. PCT/US16/37795.
Non-Final Office Action dated May 17, 2018 from U.S. Appl. No. 15/081,096, 12 pages.
Final Office Action dated Jan. 7, 2019 from U.S. Appl. No. 15/081,096, 13 pages.
Non-Final Office Action dated May 29, 2019 from U.S. Appl. No. 15/081,096, 17 pages.

* cited by examiner

200

```
┌─────────────────────────────────────────────────────────────────────────┐
│ Sensing an indication of deformation in a fluid reservoir formed at least partly │
│ within an insole, when the insole is disposed under the foot of a user, the fluid │
│                         reservoir containing a fluid                    │
│                                    210                                  │
└─────────────────────────────────────────────────────────────────────────┘
                                    │
                                    ▼
┌─────────────────────────────────────────────────────────────────────────┐
│ Transmitting deformation information based on the indication of deformation to │
│                              a remote device                            │
│                                    220                                  │
└─────────────────────────────────────────────────────────────────────────┘
```

FIG. 2

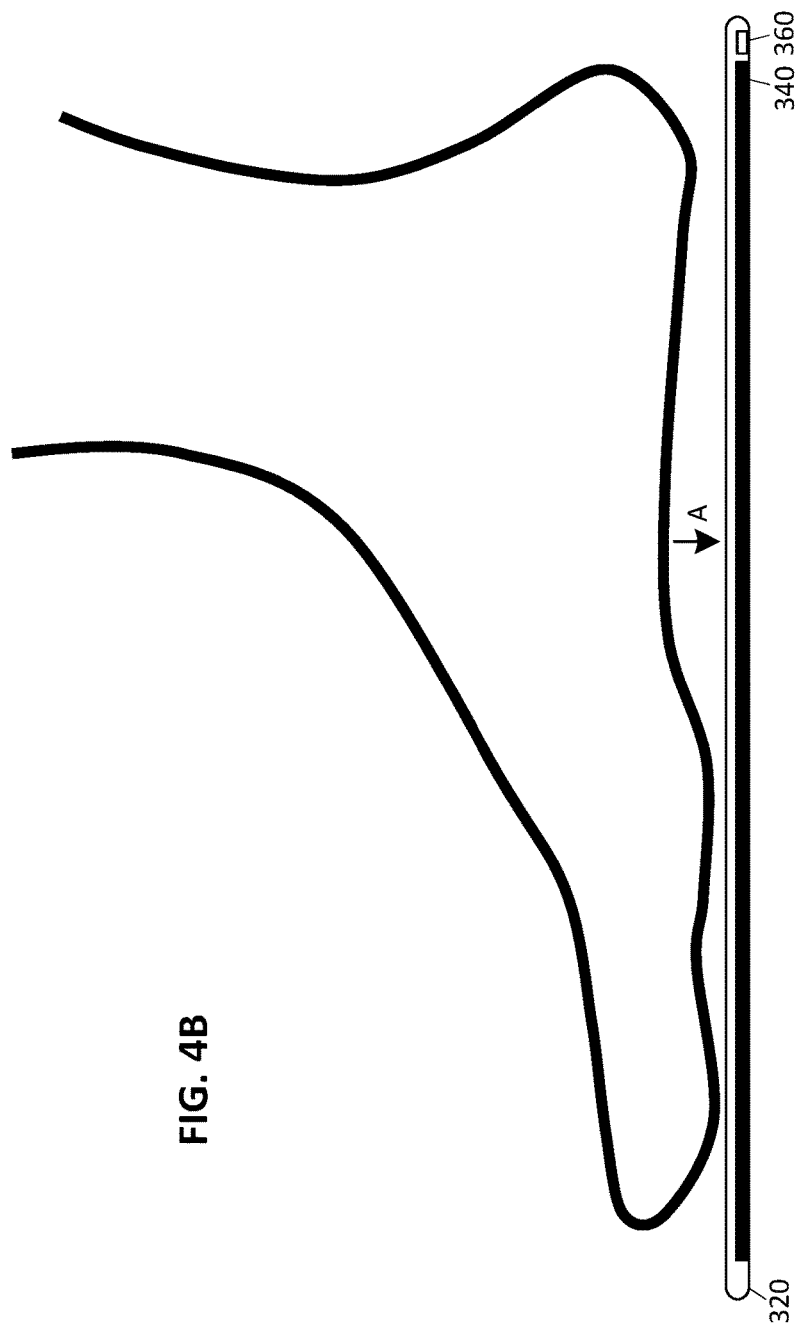
FIG. 4A
FIG. 4B

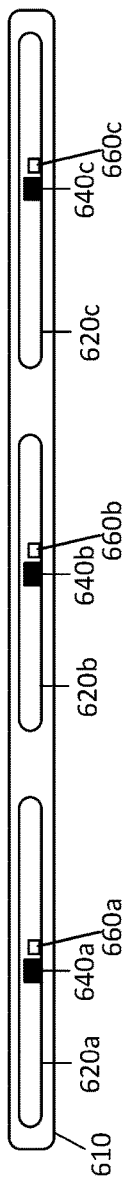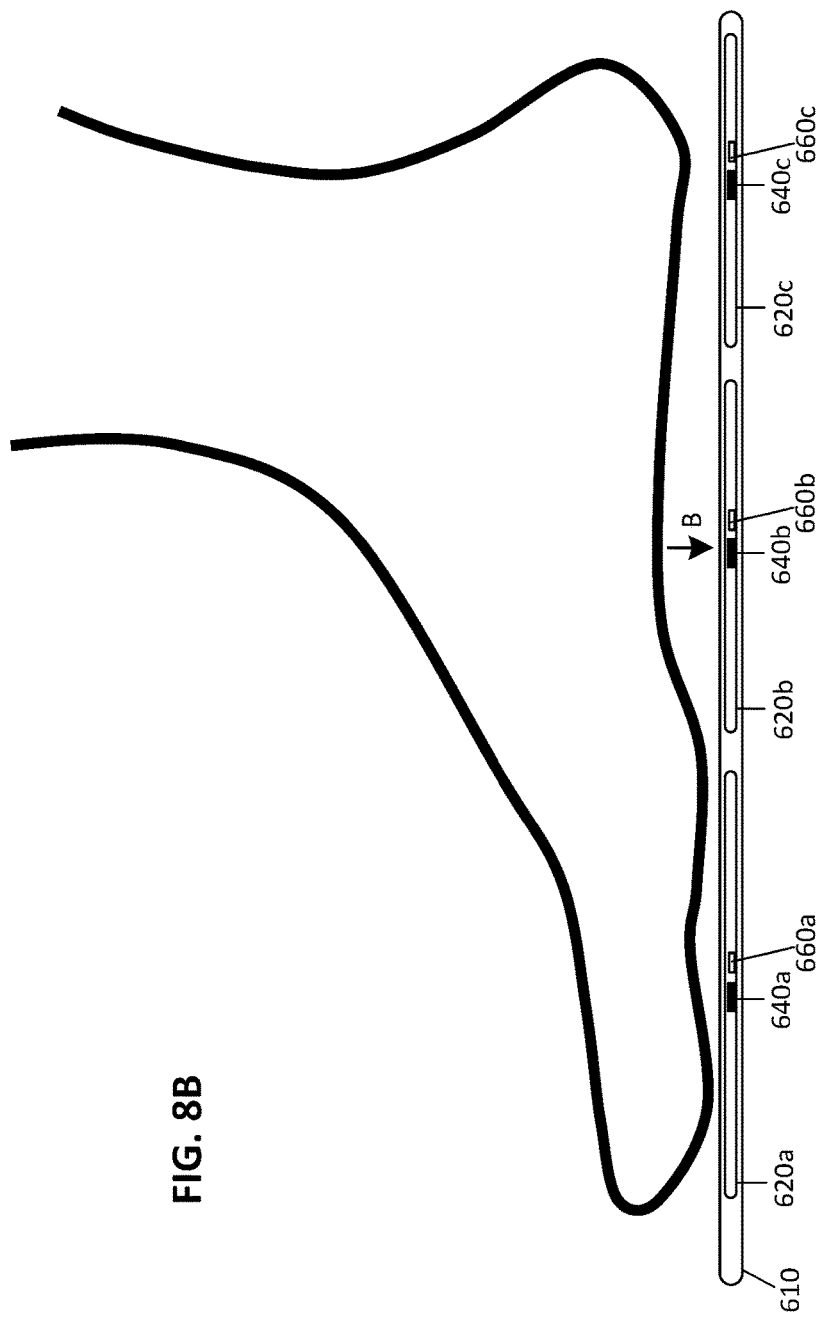
FIG. 8A
FIG. 8B

APPARATUSES, METHODS, AND SYSTEMS FOR MEASURING INSOLE DEFORMATION

CROSS-REFERENCE TO RELATED APPLICATIONS

This application claims priority to and the benefit of U.S. Provisional Application No. 62/180,428 entitled "APPARATUSES, METHODS, AND SYSTEMS FOR MEASURING INSOLE DEFORMATION," filed Jun. 16, 2015, the disclosure of which is incorporated herein by reference in its entirety.

BACKGROUND

A steady stream of medical studies has recently shown a strong correlation between fitness and activity to overall personal health leading to rising demand for devices that can track a number of metrics, including the number of steps taken, activity levels, heart rate, quality and length of sleep, calories burned, etc. These "fitness trackers" are rapidly increasing in popularity, both with individuals that are trying to stay fit, and with those who have serious health issues and are looking for motivation to get healthier. By tracking metrics and daily habits, a user can identify trends and adjust their habits and lifestyles accordingly. Furthermore, with the increased popularity and improved capabilities of smart phones, users are able to connect multiple devices with applications running on a smart phone to aggregate data from numerous sources.

Fitness trackers are often worn around the user's wrist, chest, or waistband, which are ideal locations for measuring the user's pulse and steps taken. However, because of the location and/or position on the user's body, these devices are not capable of measuring some important biometric parameters such as, for example, a user's weight. A user's weight can closely correlate to risk factors for some serious diseases, such as high blood pressure, high cholesterol, heart disease, etc. The most common way to measure weight gain or loss is for an individual to step on a scale (e.g., either in a doctor's office or at home) and then track weight gain or loss over time. However, when using a personal scale, users can choose when to weigh themselves, and can even avoid the scale when they know they have gained a few pounds. Additionally, while some users may write down their weight, many users do not track the change in any formal way. Recently, some bathroom scales have become WiFi or Bluetooth enabled, which allows a user's weight to be sent to a smartphone or other device for weight tracking purposes, however, the user still has to step on the scale to initiate the measurement. Thus, when the user avoids the scale or forgets to use it, there can be large gaps in data and/or insufficient data to show an accurate trend in the user's weight.

Attempts have been made to use shoe insoles with capacitive sensors to measure a user's weight, but these capacitive sensors can be problematic for a number of reasons. For example, capacitive sensors typically have two parallel plates that work best for measuring a force normal to the plane of the plates. Thus, the weight measurement determined when the user stands straight on the insole may be accurate, but the capacitive sensors provide inaccurate, erroneous readings if the plates are misaligned (i.e., if they are not in a parallel relationship). Based on the nature of walking, running, and sporting activities such as basketball, football, baseball, figure skating, and the like, the force on the insole is rarely normal to the insole, which leads to a data set that has a very weak correlation to the user's actual weight. Furthermore, one strong force or repeated shear forces can cause the capacitive plates to become misaligned, thereby causing permanent damage to the sensors resulting in inaccuracies in all of the weight measurements taken anytime thereafter. Yet another problem arises because these discrete capacitors only record a small cross-section of the total downward force. For example, smart insoles often employ several sensors placed in locations where there is more downward force, such as regions that correspond to a user's heel, ball, and toe regions. As a result, the sensors only obtain a partial recording of the downward force, thus failing to record the total force distributed over the entire foot and in all directions and orientations.

SUMMARY

Apparatuses, devices, and methods for measuring insole deformation are described herein. In some embodiments, a device includes an insole configured to be disposed under a foot of a user during use. The device further includes a fluid reservoir formed at least partly within the insole, the fluid reservoir containing a fluid. The device further includes a sensor fluidically coupled to the fluid reservoir and configured to sense an indication of deformation in the fluid reservoir during use. The device also includes a communications component communicatively coupled to the sensor and configured to receive the indication of deformation from the sensor. The communication component is further configured to transmit deformation information associated with the indication of deformation to a remote device.

In some embodiments, a method includes sensing an indication of deformation in a fluid reservoir formed at least partly within an insole, when the insole is disposed under the foot of a user and the fluid reservoir contains a fluid. The method further includes transmitting deformation information based on the indication of deformation to a remote device.

In some embodiments, a kit includes a pair of footwear, and a device. The device includes an insole configured to be disposed under the foot of a user during use. The device further includes a fluid reservoir formed at least partly within the insole, the fluid reservoir containing a fluid. The device further includes a sensor fluidically coupled to the fluid reservoir and configured to sense an indication of deformation in the fluid reservoir during use. The device also includes a communications component communicatively coupled to the sensor and configured to receive the indication of deformation from the sensor. The communication component is further configured to transmit deformation information associated with the indication of deformation to a remote device.

In some embodiments, a kit includes a first device, the first device being wearable by a user. The kit also includes second device that includes an insole configured to be disposed under the foot of the user during use. The second device further includes a fluid reservoir formed at least partly within the insole, the fluid reservoir containing a fluid. The second device further includes a sensor fluidically coupled to the fluid reservoir and configured to sense an indication of deformation in the fluid reservoir during use. The second device also includes a communications component communicatively coupled to the sensor and configured to receive the indication of deformation from the sensor. The communication component is further configured to transmit deformation information associated with the indication of deformation to the first device.

BRIEF DESCRIPTION OF THE DRAWINGS

FIG. 2 is a method for insole deformation measurement, according to an embodiment.

FIG. 4A is a side view of the insole of FIG. 3 in a first configuration.

FIG. 4B is a side view of the insole of FIG. 3 in a second configuration.

FIG. 8A is a side view of the insole of FIG. 7 in a first configuration.

FIG. 8B is a side view of the insole of FIG. 7 in a second configuration.

DETAILED DESCRIPTION

Figure 1:
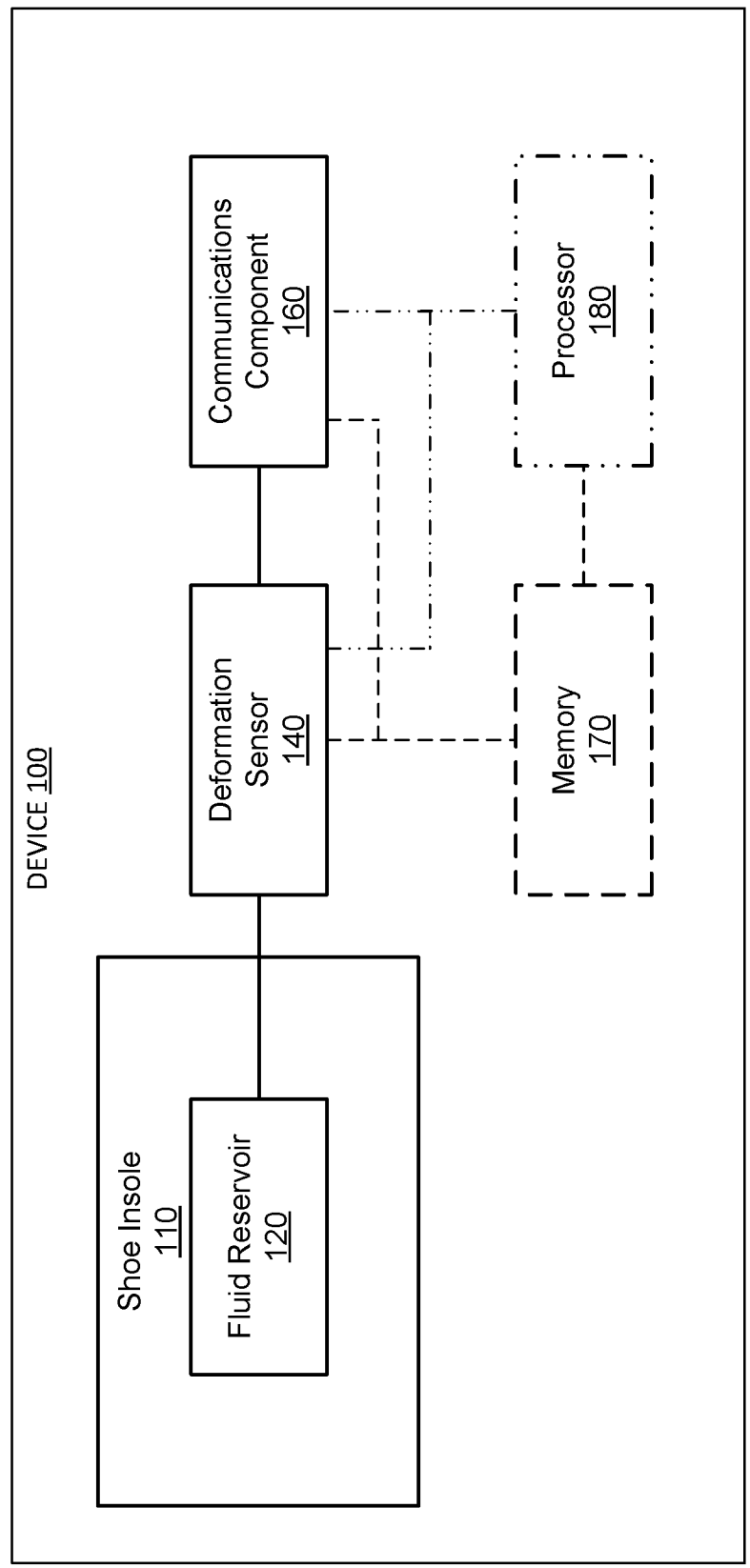
FIG. 1 is a schematic block diagram of an insole for measuring the weight of a user, according to an embodiment.

Apparatuses, devices, and methods for measuring deformation in an insole, such as, for example, for determining the weight of a user, are described herein.

Weight can be an important metric when determining health and wellbeing of an individual. In particular, weight can be an important factor in determining the user's body mass index (BMI), and can be indicative of risk factors for certain diseases and conditions, such as high blood pressure, high cholesterol, heart disease, and the like. Additionally, rapid changes in weight can be an early indication for some serious diseases such as, for example, pancreatic cancer and congestive heart failure. As described herein, individuals can track their own weight by regularly using a bathroom scale, however, users often forget to weigh themselves, avoid regular weigh ins, and/or do not track their weight over time. Even though some newer model bathroom scales can wirelessly transmit the user's weight to a remote device (e.g., a smart phone or personal computer), users still decide when to use those scales leading to inconsistent and/or inaccurate data. Lack of a consistent track record of an individual's weight thus fails to show any meaningful trend of that individual's health metrics over time, which can result in a failure to recognize a rapid weight change that can be indicative of a serious disease.

As part of a recent trend to improve health and fitness, devices have been developed to track steps taken, activity levels, heart rate, sleep metrics, calories burned, etc. These devices are often worn around a user's wrist, chest, or waistband, and are often referred to as "fitness trackers," "activity monitors," or "wearables." Wearables have rapidly grown in popularity as many people have developed an increased interest in their health and wellbeing. A variety of metrics can be tracked by wearables, and these metrics can then be transferred to a user's device, such as a smart phone, tablet, or personal computer. This allows users to view trends in these metrics, and adjust their lifestyle accordingly. Although some attempts have been made to track a user's weight using capacitive sensors in insoles, these sensors have a number of flaws, therefore, there is a need for a new wearable sensor that allows a user to accurately and easily track weigh gain and/or loss over time.

As used herein, the word "fluid" is used to indicate air, liquid, gas, foam, fluid gels, combinations thereof, and/or any other material/medium used within a bladder of the insole.

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are discontinuous from each other. A set of walls can also be fabricated from multiple items that are produced separately and are later joined together (e.g., via a weld, an adhesive and/or any suitable method).

The terms "about," "approximately," and "substantially" as used herein in connection with a referenced numeric indication means the referenced numeric indication plus or minus up to 10% of that referenced numeric indication. For example, the language "about 50" units or "approximately 50" units means from 45 units to 55 units. Such variance can result from manufacturing tolerances or other practical considerations (such as, for example, tolerances associated with a measuring instrument, acceptable human error, or the like).

In some embodiments, a device includes an insole configured to be disposed under a foot of a user during use. The device further includes a fluid reservoir formed at least partly within the insole, the fluid reservoir containing a fluid. The device further includes a sensor fluidically coupled to the fluid reservoir and configured to sense an indication of deformation in the fluid reservoir during use. The device also includes a communications component communicatively coupled to the sensor and configured to receive the indication of deformation from the sensor. The communication component is further configured to transmit deformation information associated with the indication of deformation to a remote device.

FIG. 1 is a schematic illustration of a device 100 (also sometimes referred to as an "apparatus") including an insole 110 configured to be disposed under the foot of a user (not shown) during use, according to an embodiment. The insole 110 can be any of a variety of sizes and shapes, and can be integrally formed with footwear (e.g., a shoe) during a manufacturing process, can be included as a separate component with footwear when the footwear is purchased, or can be sold separately from the footwear. The insole 110 can be made from one or more materials, such as foam, neoprene, plastic, rubber, gel, combinations thereof, and/or the like. In some embodiments, the insole 110 can be made using an odor absorbent material and/or can be coated with an odor absorbent material.

In some embodiments, the insole 110 can be configured to fit a specific user such that the insole 110 is customized for that user. In some embodiments, the insole 110 can be configured to fit a specific footwear size, shoe brand, shoe type, and/or the like. In some embodiments, the insole 110 can be made in one or more standard sizes (e.g., small, medium, large, etc.), and the user can trim the outer edges of the insole 110 to make the insole 110 fit into the footwear of their choice. Thus, one insole 110 can be configured to fit several footwear sizes. For example, one size insole can be configured to fit a men's size 6-8 shoe and a women's size 7-9 shoe. The insole 110 may be sized initially to fit a men's size 8 and a women's size 9, but the insole 110 can be cut or otherwise reshaped to fit shoes as small as a men's size 6 and a women's size 7 without damaging the shoe insole 110. In some embodiments, the smallest acceptable size (i.e., the minimum size to which a user can trim the insole 110 to) can be marked on the insole such that the user does not damage other portions of the insole, such as a fluid reservoir or electronics.

In some embodiments, a user can have one insole 110 that the user transfers between different pairs of footwear, such as, for example, between different pairs of shoes, between a pair of heels and a pair of shoes, and/or the like. In some embodiments, the user can have one insole 110 that stays in a single pair of shoes that the user wears regularly, such as sneakers that the user wears to commute, or to run daily. In other embodiments, the user can have multiple insoles 110 that are in different shoes. The insole 110 can take various shapes, and can be configure to fit in different types of shoes. For example, the insole 110 can be configured to fit into a pair of sneakers, a pair of dress shoes, a pair of flats, a pair of heels, and/or the like. The user can have an insole 110 in each shoe or have an insole configured to be placed in each type of shoe.

As illustrated in FIG. 1, the device 100 further includes a fluid reservoir 120, a deformation sensor 140, and a communications component 160. The device 100 can also optionally include a memory 170 and/or a processor 180, as indicated by dashed lines in FIG. 1. In some embodiments (not shown), the device 100 further includes a database. In some embodiments (not shown), the device 100 can further include a power source, such as, but not limited to, replaceable batteries such as button cells, an integrated battery, a rechargeable battery (including an inductively-rechargeable battery), capacitors, super-capacitors, and/or the like.

The memory 170 and/or the database of the device 100 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. In some embodiments, instructions associated with performing the operations described herein (e.g., body weight calculation) can be stored within the memory 170 and executed at the processor 180. The processor 180 can be, for example, a general purpose processor, a Field Programmable Gate Array (FPGA), an Application Specific Integrated Circuit (ASIC), a Digital Signal Processor (DSP), and/or the like. The processor 180 can be configured to run and/or execute application processes and/or other modules, processes and/or functions associated with the device 100. In some embodiments, the processor can include one or more components/modules (not shown), where each can independently be a hardware component/module and/or a software component/module. In some embodiments, each of the components/modules can be operatively coupled to each other. In other embodiments, the functionality of one or more of the components/modules can be combined and/or overlap. In some embodiments, the functionality of one or more components/modules and/or the interaction between the components/modules can be based on regulatory requirements for data processing, storage, integrity, security, and/or the like. While shown as being implemented in the processor 180, in other embodiments, the components/modules, or a portion thereof, can be distributed, and implemented in other processors and/or network devices. Such processors and/or network devices can be communicatively coupled via, for example, a network.

In some embodiments, the fluid reservoir 120 is formed at least partly within the insole 110. In some embodiments, the fluid reservoir 120 (also referred to herein as "bladder") can include a top substrate (not shown) and a bottom substrate (not shown) that are made from plastic such as polyethylene or polyurethane, neoprene, soft rubber, foam, and/or the like. In some embodiments, the top substrate and bottom substrate can be attached to each other around the outside edges to create a seal around a perimeter to form the fluid reservoir 120 and the fluid reservoir 120 can be filled with a fluid such as, for example, air, liquid, foam, and/or the like. In some embodiments, the top and bottom substrates can be made from deformation sensor material, which can include one or more of StretchSense™ material, SMARTape™, Flexi-Force® sensors, a strain gauge, a piezoresistor, a semiconductor gauge, and/or combinations thereof.

In some embodiments, the fluid reservoir 120 can be refillable by the user. In some embodiments, the fluid reservoir can include a valve (not shown) configured for filling at least a portion of the fluid reservoir with the fluid and/or draining at least a portion of the fluid from the fluid reservoir. For example, a refilling mechanism (not shown) can be used to add or remove the fluid via the valve of the fluid reservoir 120. The refilling mechanism can include a needle and/or pump or other similar refilling mechanism. In some embodiments, the refilling mechanism can be custom made to refill the fluid reservoir 120 of the device 100, and in other embodiments, the refilling mechanism can be a standard refilling mechanism similar to that used to refill a basketball, etc. In some embodiments, the fluid reservoir 120 is not refillable by a user.

In some embodiments, the device 100 can include a single fluid reservoir 120. When the device 100 includes a single fluid reservoir 120, the fluid reservoir 120 can be substantially the same shape as the insole 110 and can occupy substantially the entire interior of the insole 110.

In some embodiments, the device 100 can include multiple fluid reservoirs 120. In some embodiments, the device 100 can include a single fluid reservoir 120 that is subdivided into multiple portions or compartments (not shown). Standing on a single fluid reservoir 120 may feel unstable, as it can feel like standing on a balloon of air or liquid. Decreasing the volume of fluid in the reservoir 120 can help reduce the sensation of standing on a balloon, but a single reservoir still has the potential of imparting instability to the shoe insole 100. Alternatively, the fluid reservoir 120 can include multiple portions, and at least a first portion and a second portion of the multiple portions are in fluid communication with each other. In some embodiments, the fluid reservoir 120 includes multiple portions, and at least a first portion and a second portion of the multiple portions are fluidically isolated from each other. In some embodiments, the fluid reservoir 120 can include multiple portions, and a first portion of the multiple portions is made from a different material than a second portion of the multiple portions. In some embodiments, the fluid reservoir 120 can include multiple portions, and a first portion of the multiple portions at least partly overlays a second portion of the multiple portions during use.

In some embodiments, the fluid reservoir 120 can occupy less than the majority of the interior of the insole 110 to help increase stability. For example, the fluid reservoir 120 can occupy the heel portion of the insole 110. In some embodiments, the insole 110 includes multiple fluid reservoirs 120, and/or the fluid reservoir 120 is divided into multiple portions, leading to increased stability and accuracy of resulting measurements, such as, for example, body weight measurements based on the deformation in the fluid reservoir(s) 120.

For example, in some embodiments, the fluid reservoir 120 can be "quilted" to subdivide the fluid reservoir 120 into multiple portions that are in fluid communication with each other. This can be accomplished in several ways, such as by connecting, at various predetermined locations, the top substrate of the fluid reservoir 120 to the bottom substrate of the fluid reservoir 120. For example, in some embodiments, relatively small, discrete, intervals of the top and bottom portions can be connected to one another in a predetermined pattern such that fluid can pass from one section within the fluid reservoir 120 to another section between these connected portions. In some embodiments, relatively larger portions of the top and bottom substrates of the fluid reservoir 120 can be connected to one another, but at further distances from each other. In some embodiments, supports can be positioned between the top and bottom substrates at predetermined locations, such that the top substrate and the bottom substrate are connected through the supports, while the fluid can move freely around the supports within the fluid reservoir 120. In some embodiments, the interior of the bladder is filled with an open-cell foam, which can allow fluid to move through the cells. The foam can optionally be adhered to at least one of the top or bottom substrate of the fluid reservoir 120, but can also be unattached. In some embodiments, the foam portion can be smaller than the fluid reservoir 120, which can also be configured to provide support in some places. In other embodiments, the foam can cover substantially all of the interior area of the bladder 120. Any combination of the embodiments described herein for subdividing the fluid reservoir 120 can be used to increase the stability of the insole 110.

As described herein, multiple fluid reservoirs 120 can be used to increase the stability of the device 100. In some embodiments, the fluid reservoir 120 can include multiple portions, at least one portion of the multiple portions formed under the ball of foot of the user during use. In some embodiments, at least a portion of the fluid reservoir can be formed under the ball of foot of the user during use. In some embodiments, the fluid reservoir can include multiple portions, and at least one portion of the multiple portions can be formed under the arch of foot of the user during use. In some embodiments, at least a portion of the fluid reservoir can be formed under the arch of foot of the user during use. In some embodiments, the fluid reservoir can include multiple portions, and at least one portion of the multiple portions can be formed under the heel of foot of the user during use. In some embodiments, at least a portion of the fluid reservoir can be formed under the heel of foot of the user during use. For example, in some embodiments, three bladders (i.e., distinct fluid reservoirs) can be included in the device 100: a first fluid reservoir (not shown) near the front of the insole 110 and configured to be positioned under the ball of the user's foot; a second fluid reservoir (not shown) near the middle of the insole 110 and configured to be positioned under the user's arch; and a third fluid reservoir near the back of the insole 110 and configured to be positioned under the user's heel. In some embodiments, more or fewer reservoirs can be included to increase the stability of the device 100 and/or otherwise optimize the weight sensing or other capabilities of the device 100. Furthermore, any or all of the fluid reservoir(s) 120 can be further subdivided as described above with perforations, and/or the like.

In some embodiments, multiple fluid reservoirs 120 can provide some additional flexibility and/or functionality. For example, at least one of the fluid reservoirs 120 can be filled to different capacities or with different fluids than another one of the fluid reservoirs 120. In some embodiments, the user can determine which of the fluid reservoirs 120 to fill, the extent to which to fill the fluid reservoirs 120, and/or with what specific fluid/combination of fluids to fill the fluid reservoirs 120. In some embodiments, the fluid reservoirs 120 can have a second functionality such as, for example, as an orthotic. For example, for a user with flat feet, a fluid reservoir of the fluid reservoirs 120 under the user's arch can be filled such that the fluid reservoir also adds support for the user's arch. In some embodiments, each of the fluid reservoirs 120 can be made from different materials. For example, a fluid reservoir of the fluid reservoirs 120 disposed under the user's heel during use may require reinforcement because of the additional force incurred when the user's heel hits the insole (as compared with the user's arch, for example). By having multiple fluid reservoirs, a different material (or the same material with extra reinforcement) can be used under the user's heel, under the user's arch, and/or under the ball of the user's foot. In some single fluid reservoir implementations, however, the material can be varied in different parts of the fluid reservoir 120. For example, the reservoir material may be thicker under the user's heel than under the user's arch.

When the user stands on the fluid reservoir 120, the force applied to the fluid reservoir 120 can be measured by determining the deformation in the fluid reservoir 120 and/or the deformation variation of the fluid reservoir 120, regardless of the angle of the force. For example, when a user steps on the insole 110, a force proportional to the user's weight is exerted on the fluid reservoir 120 regardless of the direction of approach, orientation of the foot, or the speed/rate of the stepping action, and the deformation of the fluid reservoir 120 can be used to determine the weight of the user. In such instances, a deformation sensor 140 coupled to or placed on, in, or within the fluid reservoir 120 can measure the deformation and/or change in the deformation of the fluid reservoir 120, and values related to the absolute deformation, relative deformation, and/or the change in deformation can be used to determine metrics, such as the user's weight. In some embodiments, one or more deformation sensors 140 can be disposed within, attached to, fluidically coupled to, placed in, and/or otherwise connected to the fluid reservoir 120 to provide additional data points which can be combined and/or analyzed in any suitable approach to provide a more robust data set for determining the user's weight. In some embodiments, one or more deformation sensors 140 can be placed as desired by the user, e.g., near a user-specified location of one or more fluid reservoirs 120, and used for measuring the deformation in the fluid reservoirs 120.

In some embodiments, the top and/or bottom substrates of the fluid reservoir 120 can be made from deformation sensor material. The deformation sensor 140 can measure the deformation of the fluid reservoir 120, and the measured deformation can be correlated to a weight measurement of the user. In some embodiments, the deformation sensor 140 measures a change in deformation of the bladder 120, and the change in deformation correlates to a weight measurement of the user. The deformation sensor 140 can be StretchSense™ material, SMARTape™, FlexiForce® sensors, a strain gauge, a piezoresistor, a semiconductor gauge, and/or the like.

In some embodiments, the deformation sensor 140 is configured to sense an indication of deformation in at least one of the first portion and the second portion. In some embodiments, the deformation sensor 140 is fluidically coupled to the first portion of the multiple portions and is further configured to sense the indication of deformation in the first portion. In some embodiments, a second sensor (not shown) is fluidically coupled to a second portion of the multiple portions of the fluid reservoir to sense an indication of deformation in the second portion.

In some embodiments, an indication of deformation can include an indication of one or more of absolute deformation, absolute deformation change, gauge deformation, and gauge deformation change. In some embodiments, the indication of deformation can include uniaxial deformation (e.g., when a uniaxial strain gauge is used) or multi-axial deformation (e.g, when a bi-axial strain gauge is used). In some embodiments, the sensor 140 can be further configured to sense a temperature of the fluid reservoir, or in the proximity thereof. In some embodiments, the sensor 140 can be further configured to sense a temperature of the insole, or in the proximity thereof. In some embodiments, the sensor 140 is a first sensor, and a second sensor can be configured to sense a temperature of the fluid reservoir, or in the proximity thereof. In some embodiments, the sensor 140 is a first sensor, and a second sensor can be configured to sense a temperature of the insole, or in the proximity thereof. In some embodiments, one or more additional sensors are fluidically coupled to the fluid reservoir to sense additional indications of deformation in the fluid reservoir during use.

The sensor 140 can measure an indication of deformation and the deformation can be the basis for and/or correlated to the body weight of a user. In some embodiments, the deformation, and/or the change in deformation can be the basis for and/or correlated to a body weight of the user. In some embodiments, the sensor 140 can be a MEMS sensor, a piezoelectric sensor, an optical sensor, an electromagnetic sensor, a piezoresistive strain gauge, and/or the like.

In some embodiments, the sensor 140 can measure absolute deformation, such as measuring deformation against an internal reference, and in other embodiments, the sensor 140 can measure gauge deformation. A temperature sensor (not shown), such as a thermistor or thermocouple, can also be incorporated. Changes in temperature can occur due to the outside air temperature and/or due to body heat. Due to the correlation between temperature and deformation, the temperature inside the insole may affect the deformation measurements determined by the deformation sensor 140. The temperature sensor can be a separated unit or it can be incorporated into the deformation sensor 140. In some embodiments, the temperature sensor can be inside the fluid reservoir 120 or otherwise attached to the insole 110.

In some embodiments, a single deformation sensor 140 can be used. The deformation sensor 140 can be disposed within, attached to, fluidically coupled to, placed in, or otherwise connected to the fluid reservoir 120. In some embodiments, the top and bottom substrate of the bladder 120 can be made from deformation sensor material 140. In other embodiments, however, multiple deformation sensors 140 can be used. When multiple deformation sensors 140 are used, the multiple sensor measurements can be synchronized and/or statistically analyzed in order to accurately determine the user's weight. In some embodiments, one deformation sensor 140 can be used for each fluid reservoir 120. Thus, in embodiments with multiple fluid reservoirs 120, one deformation sensor 140 can be included in the device 100 for each fluid reservoir 120. Multiple deformation sensors 140 can also be used with each fluid reservoir 120.

In some embodiments, the deformation sensor 140 can be a plane and/or direction-sensitive sensor and provide a measurement based on one or more pre-determined planes and/or directions of deformation. In such embodiments, the deformation sensors 140 can determine the weight of a user when the deformation takes place in the given plane(s) or direction(s) of deformation. For example, in some embodiments, the deformation sensor 140 can be a uniaxial strain gauge which detects deformation and provide information for deformation in one direction, as determined by the uniaxial strain exerted along the one direction in the deformation sensor 140. If the user steps on the fluid reservoir 120 or the insole 110 at an improper angle or in an improper direction, if the user's feet are either too large or too small, and/or the user's feet are different from the intended size, the weight of user's might not be properly measured. In some embodiments, the measurement of the weight can be linearized so that the weight distribution can be transposed onto a longitudinal direction, and summed in that direction to provide the overall weight measurement. The use of uniaxial strain gauge can aid in determining relatively more accurate weight measurement for users with high-arching feet. Although the deformation profile (e.g., footprint) created by a high-arching foot may not be linear, the deformation itself can be projected onto a single direction (i.e., along the length of the foot) for measurement of user's weight, independently of the deformation profile of the foot print.

In some embodiments, the deformation sensor 140 can be a bi-axial, plane and/or direction-agnostic sensor, which measures the overall deformation of the sensing area of the fluid reservoir 120. In some embodiments, the deformation sensor 140 can measure the deformation of the insole 110 in the absence of the fluid reservoir 120. In some embodiments, the deformation sensor 140 used to measure the deformation of the insole 110 is a plane or direction-sensitive sensor, such as a uniaxial strain gauge. In some embodiments, the deformation sensor 140 used to measure the deformation of the insole 110 is a bi-axial, plane or direction-agnostic sensor, such as a multi-axial strain gauge.

In some embodiments, additional sensors 140 can be used to determine an average deformation and/or average deformation change, and this average can be the amount used to determine the weight of the user. The additional sensors 140 can also be used as backup if one of the deformation sensors 140 stops working properly. For example, if the sensors detect substantially different deformation and/or deformation values, a determination can be made as to which sensor is producing a faulty reading, and measurements from that deformation sensor can be disregarded. In some embodiments, when multiple deformation sensors 140 are used, each deformation sensor can be tracked independently, and these measurements can be synchronized and/or statistically analyzed. In some embodiments, this analysis can be used to determine a time-varying measurement of the user's gait.

Once a deformation measurement is taken, the deformation and/or deformation change can be stored, e.g., in the memory 170, at least temporarily, and the stored measurement can be communicated to a remote device (e.g., a user's device), such as a cell phone, computer, tablet, fitness device, and/or the like. In some embodiments, the remote/user device can include a device for dynamic control, as generally disclosed in U.S. application Ser. No. 14/881,677 titled "SYSTEMS, DEVICES, AND METHODS FOR DYNAMIC CONTROL", filed Oct. 13, 2015, the entire disclosure of which is incorporated herein by reference. In some embodiments, the remote/user device can include a device for representing facial expressions and/or indications of activity, as generally disclosed in U.S. application Ser. No. 14/336,064 titled "METHODS AND SYSTEMS FOR DISPLAYING REPRESENTATIONS OF FACIAL EXPRESSIONS AND ACTIVITY INDICATORS ON DEVICES", filed Jul. 21, 2014, the entire disclosure of which is incorporated herein by reference. In some embodiments, the remote/user device can include a device configured for data transfer as generally disclosed in U.S. application Ser. No. 14/309,195 titled "SYSTEMS AND METHODS FOR DATA TRANSFER", filed Jun. 19, 2014, the entire disclosure of which is incorporated herein by reference.

The measurement can be stored and transmitted to the user device using the communications component 160, which can be disposed within or attached to the device 100. The communications component 160 can receive readings from the deformation sensor 140 and transmit the readings to a remote/user device. As described herein, in some embodiments, the device 100 can also include the processor 180 and the memory 170. The memory 170 can be configured to store a number of measurements taken by the deformation sensors 140. In some embodiments, the memory 170 may be able to store the measurements data locally within the device. These measurements can then be communicated to the remote/user device via the communications component 160 when the remote device is available for transfer.

In some embodiments, the processor 180 can be configured to generate, based on the indication of deformation, an indication of a body weight of the user, and the communication component 160 can be configured to transmit body weight information based on the indication of the body weight of the user. In some embodiments, the memory 170 can be configured to store body weight information based on the indication of the body weight of the user. In some embodiments, the sensor 140 can include one or more of StretchSense™ material, SMARTape™, FlexiForce® sensors, a strain gauge, a piezoresistor, a semiconductor gauge, a microelectromechanical system (MEMS) sensor, a piezoelectric sensor, an optical sensor, an electromagnetic sensor, a piezoresistive strain gauge, and combinations thereof.

The communications component 160 can be configured to transmit the measurements using one or more wireless technology standards, such as Bluetooth, WiFi, RFID, ANT+, ZigBee, and/or the like. In some embodiments, the communications component 160 can be configured to transmit the measurements via a network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

In some embodiments, the communications component 160 can be configured to store the raw sensor data received from the sensor 140 in the memory 170. Said another way, the sensor 140 can measure an indication of deformation and/or deformation change, and the indication of deformation and/or deformation change can be stored in the memory 170. In some embodiments, the communications component 160 can be configured to determine, via the processor 180, an indication of the weight of the user based on the deformation and/or deformation change measurements. In some embodiments, the memory 180 can be configured to store the indication of the weight of the user. In some embodiments, the memory 170 can store both the indication of the weight of the user and the indication of deformation and/or deformation change. In some embodiments, the communications component 160 can be configured to communicate with the memory 170 to transfer an indication of both the sensor data and the body weight of the user to the remote device. In other embodiments, the memory 170 can be configured to store only the indication of body weight of the user, and the communications component 160 can be configured to transfer body weight information based on the indication of body to the remote device.

In some embodiments, the sensor(s) 140 can be used to determine other metrics in addition to or instead of weight. For example, the data collected by the sensor 140 can be used to determine foot strike, gait analysis, footsteps, pace, stride length, combinations thereof, and/or the like. In some embodiments, the data collected by the sensor 140 can be used to perform foot deformation analysis. A foot deformation analysis can be determined using the deformation measurements, where the larger deformation measurement correlates to an area of more foot deformation than a smaller deformation measurement. In some embodiments, the deformation data collected by the sensor 140 can be used to determine whether a runner (for example) is running heel-to-toe or toe-to-heel. In some embodiments, the data collected by the sensors 140 can be used to determine whether a user needs orthotics or what type of orthotics a user needs based on a foot deformation analysis. In some embodiments, the data collected by the sensor 140 can be used to measure balance and weight distribution, including determining whether the user's weight is balanced evenly between the left and right leg based on sensor data from a device 100 under each of the user's feet.

In some embodiments, the communications component 160 can be configured to detect when the remote device is available for transfer. This can be referred to as an active communications module. In some embodiments, the remote device can be configured to initiate the transfer of data. In such embodiments, the communications component 160 is passive, and the remote device can send a signal to the communications component 160 that activates the module. The communications component 160 can access the memory 170 and transmit, via the processor and communications adapter, an indication of the data stored in the memory to the remote device.

In some embodiments, when multiple deformation sensors 140 are included in the device 100, either one or multiple communications components 160 can be used. For example, one communications component 160 can be included in the device 100 for every deformation sensor 140. In other embodiments, multiple sensors 140 can be communicatively coupled to a single communications component 160. For example, each insole 110 may only include one communications component 160, regardless of how many deformation sensors 140 are included in the device 100. In some embodiments, the number of communications components 160 may correlate to the number of fluid reservoirs 120 included in the device 100, regardless of the number of deformation sensors 140 included.

In some embodiments, the sensor 140 and the communication component 160 can be coupled together to form a patch that can be moved around and/or disposed within or on the insole 110 and/or a specific fluid reservoir 120. For example, in some embodiments, the patch including the sensor 140 and the communication component 160 can be removably or substantially permanently stitched onto the insole 110 or a fluid reservoir 120. In some embodiments, the patch including the sensor 140 and the communication component 160 can be removably placed on the insole 110 or on the fluid reservoir 120 via a peelable, removable or movable attaching technique, for example, by using hook and loop fasteners (e.g., Velcro® tape), adhesive, glue, temporary glue, or any other means of temporary/reversible attachment.

In some embodiments, the sensor 140 can include a port for communicatively coupling to the communication component 160 so that if one of the sensor 140 or the communication component 160 become unusable, no longer functioning, or worn-out, the non-functioning/worn out component need only be replaced. In some embodiments, the port can be a multi-pin plug, a standard interconnect, and/or the like.

FIG. 2 illustrates a method 200 for deformation measurement, according to an embodiment. The method 200 includes, at step 210, sensing an indication of deformation associated with a fluid reservoir (e.g., in an inner or outer wall associated with the fluid reservoir) formed at least partly within an insole, when the insole is disposed under the foot of a user, the fluid reservoir containing a fluid. In some embodiments, the method further includes disposing the insole under the foot of the user.

In some embodiments, the sensing at step 210 further includes sensing the indication of deformation in at least one of the first portion and the second portion from multiple portions in the fluid reservoir, where the first portion of the multiple portions and the second portion of the multiple portions are in fluid communication with each other. In some embodiments, the sensing at step 210 further includes sensing the indication of deformation in at least one of the first portion and the second portion in multiple portions in the fluid reservoir, where the first portion of the multiple portions and the second portion of the multiple portions are fluidically isolated from each other.

In some embodiments, the fluid includes one or more of a gas, a liquid, foam, gel, and combinations thereof. In some embodiments, the method includes filling at least a portion of the fluid reservoir with the fluid. In some embodiments, the indication of deformation includes an indication of one or more of absolute deformation, absolute deformation change, gauge deformation, and gauge deformation change.

The method 200 also includes step 220, which includes transmitting deformation information based on the indication of deformation to a remote device.

In some embodiments, the method 200 further includes sensing a temperature of the fluid reservoir, or in the proximity thereof. In some embodiments, the method further includes sensing a temperature of the insole, or in the proximity thereof. In some embodiments, the method further includes sensing additional indications of deformation in the fluid reservoir when the insole is disposed under the foot of the user.

In some embodiments, the method 200 further includes generating body weight information associated with the user based on the indication of deformation. In some embodiments, the method 200 further includes generating, based on the indication of deformation, an indication of a body weight of the user, and transmitting body weight information based on the indication of the body weight of the user to the remote device. In some embodiments, the method 200 further includes storing the body weight information. In some embodiments, the method 200 further includes generating, based on the indication of deformation, one or more of the following: foot strike information, gait information, footstep information, pace information, and stride information.

Embodiments disclosed herein are further directed to one or more kits including a device for deformation measurement. In some embodiments, a kit includes a pair of footwear, and a device. The device includes an insole configured to be disposed under the foot of a user during use. The device further includes a fluid reservoir formed at least partly within the insole, the fluid reservoir containing a fluid. The device further includes a sensor fluidically coupled to the fluid reservoir and configured to sense an indication of deformation in the fluid reservoir during use. The device also includes a communications component communicatively coupled to the sensor, and configured to receive the indication of deformation from the sensor. The communication component is further configured to transmit deformation information associated with the indication of deformation to a remote device.

In some embodiments, a kit includes a first device, the first device being wearable by a user. The kit also includes a second device, the second device including an insole configured to be disposed under the foot of the user during use. The second device further includes a fluid reservoir formed at least partly within the insole, the fluid reservoir containing a fluid. The second device further includes a sensor fluidically coupled to the fluid reservoir, and configured to sense an indication of deformation in the fluid reservoir during use. The second device also includes a communications component communicatively coupled to the sensor, and configured to receive the indication of deformation from the sensor. The communication component is further configured to transmit deformation information associated with the indication of deformation to a remote device.

Figure 3:
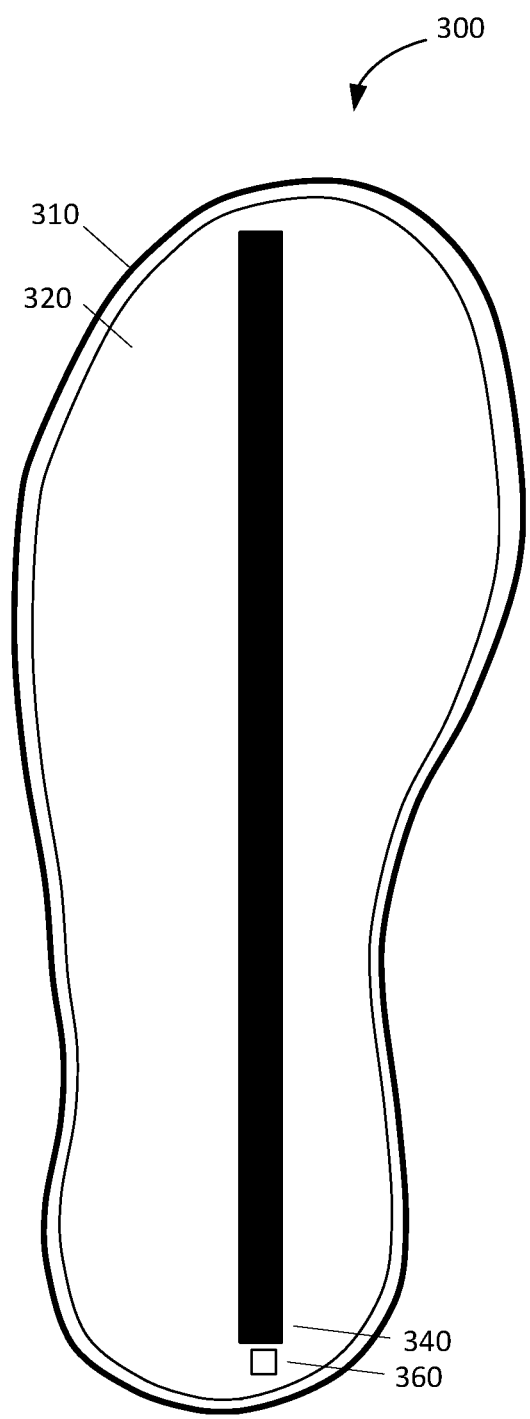
FIG. 3 is a top view of an insole for measuring the weight of a user according to an embodiment.

FIG. 3 is a top view of a device 300 for measuring the weight of a user according to an embodiment. It is noted that unless explicitly stated otherwise, similarly named and/or numbered components are structurally and or functionally similar to each other. For example, the insole 310 can be similar to the insole 110, the sensor 340 can be similar to the sensor 140, and so on.

In some embodiments, the insole 310 can be structurally and/or functionally similar to the insole 110. The insole 310 can include a single fluid reservoir 320 (e.g., structurally and/or functionally similar to the reservoir 120), and a deformation sensor 340 (e.g., similar to the deformation sensor 140) can be disposed within, attached to, fluidically coupled to, placed in, or otherwise connected to the fluid reservoir 320. A communications component 360 can be connected to the sensor 340 and can also be disposed within, attached to, fluidically coupled to, placed in, or otherwise connected to the fluid reservoir 320 and/or disposed within, attached to, coupled to, placed in, placed on, or otherwise connected to the insole 310. As illustrated in FIG. 3, in some embodiments, the fluid reservoir 320 can be substantially the same shape as the insole 310, and can occupy substantially the entire interior of the insole 310. In other embodiments (not shown), the fluid reservoir 320 can have a different shape and/or size relative to the insole 310.

Although FIG. 3 illustrates the communications component 360 as disposed near the heel area of the fluid reservoir 320, in other embodiments, the communications component 360 can be formed elsewhere relative to the fluid reservoir 320, such as, for example, below or near the arch or ball of the foot. Additionally, although the deformation sensor 340 and communications component 360 are shown in one orientation relative to the fluid reservoir 320, they can also be placed elsewhere relative to the fluid reservoir 320. Multiple deformation sensors 340 can also be placed elsewhere along the fluid reservoir 320. In some embodiments, the deformation sensor 340 can be different shapes and sizes. For example, the deformation sensor 340 can be substantially circular, substantially square, substantially rectangular, or substantially triangular; it may be generally a polygon. The deformation sensor 340 can also be substantially linear. Furthermore, the deformation sensor 340 can extend the length and/or width of fluid reservoir 320, or can extend substantially the length and/or width of the fluid reservoir 320. For example, one deformation sensor 340 can extend substantially the length of the fluid reservoir 320 and another deformation sensor 340 can extend substantially the width of the fluid reservoir 320.

In some embodiments, the deformation sensor 340 and communications component 360 can be positioned next to one another, as shown in FIG. 3, or (in other embodiments) they can be positioned differently relative to one another. In some embodiments, the deformation sensor 340 and communications component 360 can be formed as a single component having the functionality of the deformation sensor 340 and the communications component 360 as described herein. In some embodiments, the communications component 360 can be formed outside the reservoir 320, and/or outside the insole 310. In some embodiments, irrespective of the location of the sensor 340 and/or the communications component 360, the communications component 360 can be communicatively coupled with the deformation sensor 340.

FIG. 4A is a side view of the device 300 of FIG. 3. The fluid reservoir 320 can have the deformation sensor 340 and the communications component 360 disposed within, attached to, fluidically coupled to, placed in, or otherwise connected to the fluid reservoir 320. In some embodiments, the deformation sensor 340 can be adhered to, attached to, coupled to, placed on, or otherwise connected to the top substrate of the fluid reservoir 320, and/or the deformation sensor 340 can be adhered to, attached to, coupled to, placed on, or otherwise connected to the bottom substrate of the fluid reservoir 320.

The fluid reservoir 320 is shown in FIG. 4A in a first, uncompressed configuration, and when a user steps on the fluid reservoir 320 of the insole, the fluid reservoir 320 deforms, and deformation within the fluid reservoir 320 increases. In some embodiments, the deformation sensor 340 can measure an uncompressed deformation measurement, and the deformation sensor 340 can detect when a deformation occurs. In some embodiments, the deformation sensor 340 can be configured such that it records deformation and/or deformation changes if and when the difference in the measured deformations meets a predetermined criterion, i.e., when it reaches above a certain threshold from the uncompressed deformation measurement. In some embodiments, the communications component 360 can be configured such that it stores (e.g., to the memory 170) and/or transmits the deformation information based on the deformation and/or deformation changes when the difference in the measured deformation meets a predetermined criterion, i.e., when it reaches above a certain threshold from the uncompressed deformation measurement.

FIG. 4B is a side view of the insole 310 of FIG. 3 and shows a force A applied to the fluid reservoir 320. In response to the force A, the fluid reservoir 320 is compressed into a second configuration. The force A can be the force applied to the fluid reservoir 320 when a user steps on the fluid reservoir 3200. In some embodiments, the fluid reservoir 320 can deform when the force A is applied. The deformation sensor 340 can register the deformation and/or deformation change caused by force A and the communications component 360 can a) store the deformation and/or deformation change measurement; and/or b) communicate the measurement to a remote device (not shown).

Figure 5:
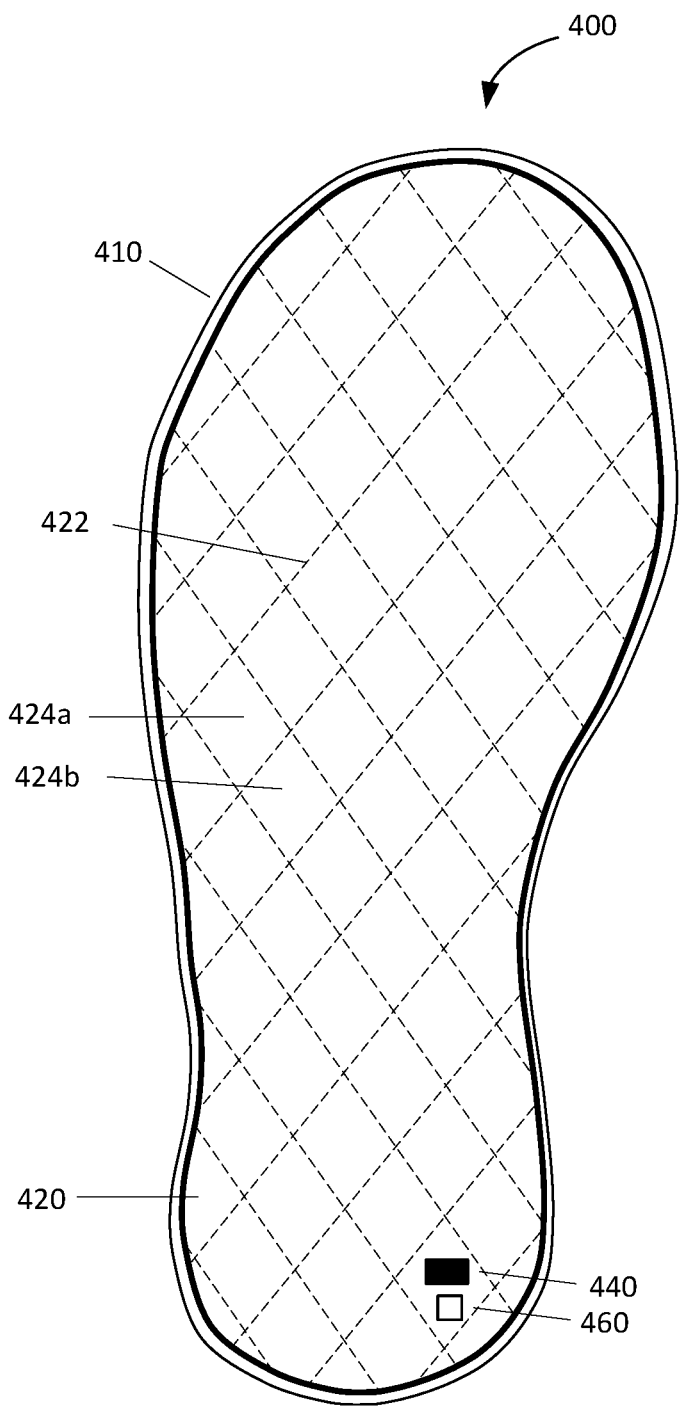
FIG. 5 is a top view of an insole for measuring the weight of a user according to an embodiment.

FIG. 5 is a top view of an embodiment of a device 400 for deformation measurement. In some embodiments, the insole 410 can be structurally and/or functionally similar to the insole 110. The device 400 includes a fluid reservoir 420 (e.g., structurally and/or functionally similar to the reservoir 120), and the fluid reservoir 420 is quilted such that a top and bottom substrate of the fluid reservoir 420 are connected in a pattern of relatively small, discrete, intervals 422. These patterned intervals 422 can create portions/chambers 424a, 424b (sometimes collectively referred to herein as "chambers 424") that are filled with the fluid of the fluid reservoir 420. The fluid can move between the chambers 424 by passing between the patterned intervals 422. When a user steps on the quilted insole 410, the deformation of the fluid within the fluid reservoir 420 increases, and the deformation and/or deformation change is measured by deformation sensor 440. These measurements, or an indication thereof, can be communicated to a remote device (not shown) using the communications component 460. In some embodiments, the device 400 and/or the remote device is configured to determine the user's body weight based on the measurements.

While the deformation sensor 440 and communications component 460 are shown in one orientation relative to the fluid reservoir 420 and chambers 424, they can also be placed and chambers 424. A deformation sensor 440 can also extend along the length and/or width of multiple chambers 424. Multiple deformation sensors 440 can also be placed elsewhere along the fluid reservoir 420. For example, in some embodiments, one deformation sensor 440 can be oriented in each chamber 424, or deformation sensors 440 can be oriented in several chambers 424 within the fluid reservoir 420. In some embodiments, the deformation sensor 440 can be different shapes and sizes. For example, the deformation sensor 440 can be substantially circular, substantially square, substantially rectangular, or substantially triangular; it may be generally a polygon. The deformation sensor 440 can also be substantially linear. Furthermore, the deformation sensor 440 can extend the length and/or width of fluid reservoir 420, or can extend substantially the length and/or width of the fluid reservoir 420. For example, one deformation sensor 440 can extend substantially the length of the fluid reservoir 420 and another deformation sensor 440 can extend substantially the width of the fluid reservoir 420. In these embodiments, the deformation sensor 440 can extend across multiple chambers 424.

Figure 6:
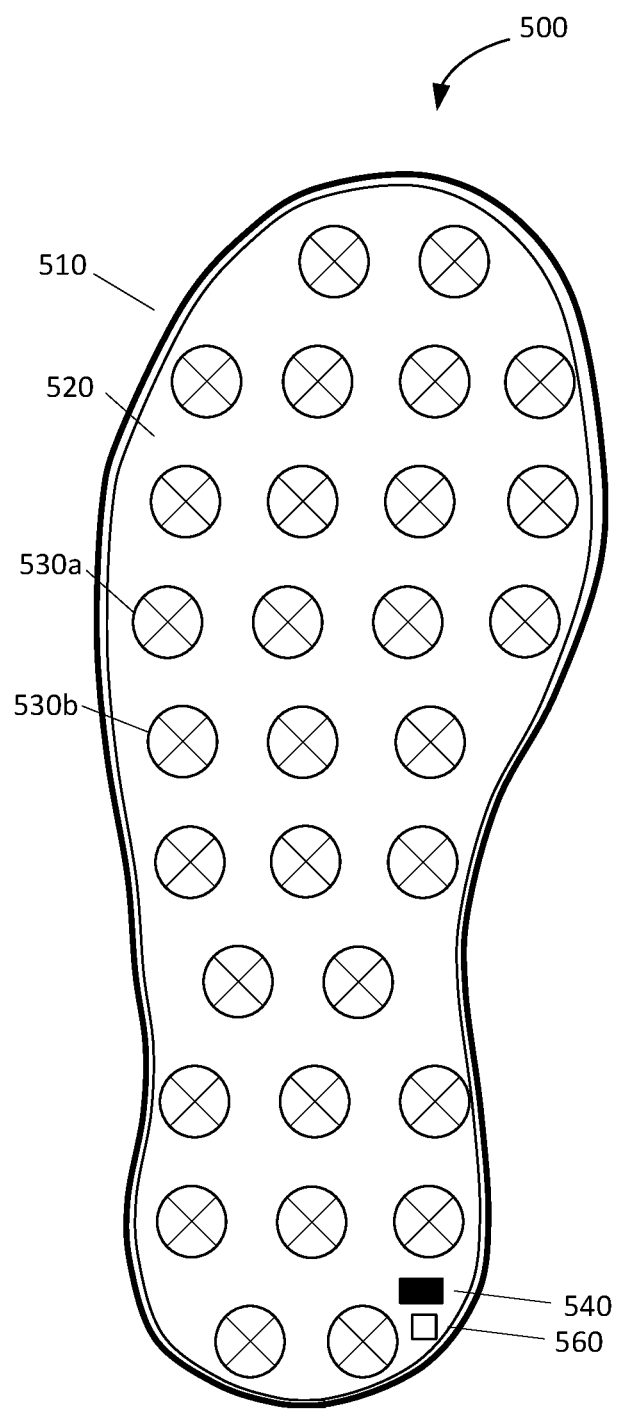
FIG. 6 is a top view of an insole for measuring the weight of a user according to an embodiment.

FIG. 6 is a top view of an embodiment of a device 500 for deformation measurement. In some embodiments, the insole 510 can be structurally and/or functionally similar to the insole 110. The device 500 includes a fluid reservoir 520 (e.g., structurally and/or functionally similar to the reservoir 120), that in turn includes a top substrate and bottom substrate. The top and bottom substrates can be connected to one another in a preset pattern. In some embodiments, the top and bottom substrates are connected to one another using supports 530a, and 530b (sometimes collectively referred to herein as "supports 530"). The supports 530 can be positioned at predetermined locations throughout the fluid reservoir 520. The fluid in the fluid reservoir 520 moves freely around the supports 530. These supports 530 can be configured to provide additional structure to the insole 510 and fluid reservoir 520. In some embodiments, the supports 530 can be areas where the first and second substrates are connected without any additional materials therebetween, and in other embodiments, the supports 530 can have additional material to provide added support. The supports 530 can be configured to be compressible, yet be rigid enough to provide structural support. When a user steps on the insole 510, the deformation within the fluid reservoir 520 increases. The sensor 540 can detect the deformation and/or deformation change, and the communications component 560 can transmit the measurements, or an indication thereof, to a remote device (not shown). In some embodiments, the device 500 and/or the remote device is configured to determine the user's body weight based on the measurements.

In some embodiments, the deformation sensor 540 can detect the deformation, and the communications component 560 can transmit the measurements While the deformation sensor 540 and communications component 560 are shown in one orientation relative to the fluid reservoir 520 and supports 530, they can also be placed elsewhere relative to the fluid reservoir 520 and supports 530. Multiple deformation sensors 540 can also be placed elsewhere along the fluid reservoir 520. In some embodiments, the deformation sensor 540 can be different shapes and sizes. For example, the deformation sensor 540 can be substantially circular, substantially square, substantially rectangular, or substantially triangular; it may be generally a polygon. The deformation sensor 540 can also be substantially linear. Furthermore, the deformation sensor 540 can extend the length and/or width of fluid reservoir 520, or can extend substantially the length and/or width of the fluid reservoir 520. For example, one deformation sensor 540 can extend substantially the length of the fluid reservoir 520 and another deformation sensor 540 can extend substantially the width of the fluid reservoir 520. In these embodiments, the deformation sensor 540 can extend across supports 530, as well as the top and/or bottom substrate of the fluid reservoir 520.

Figure 7:
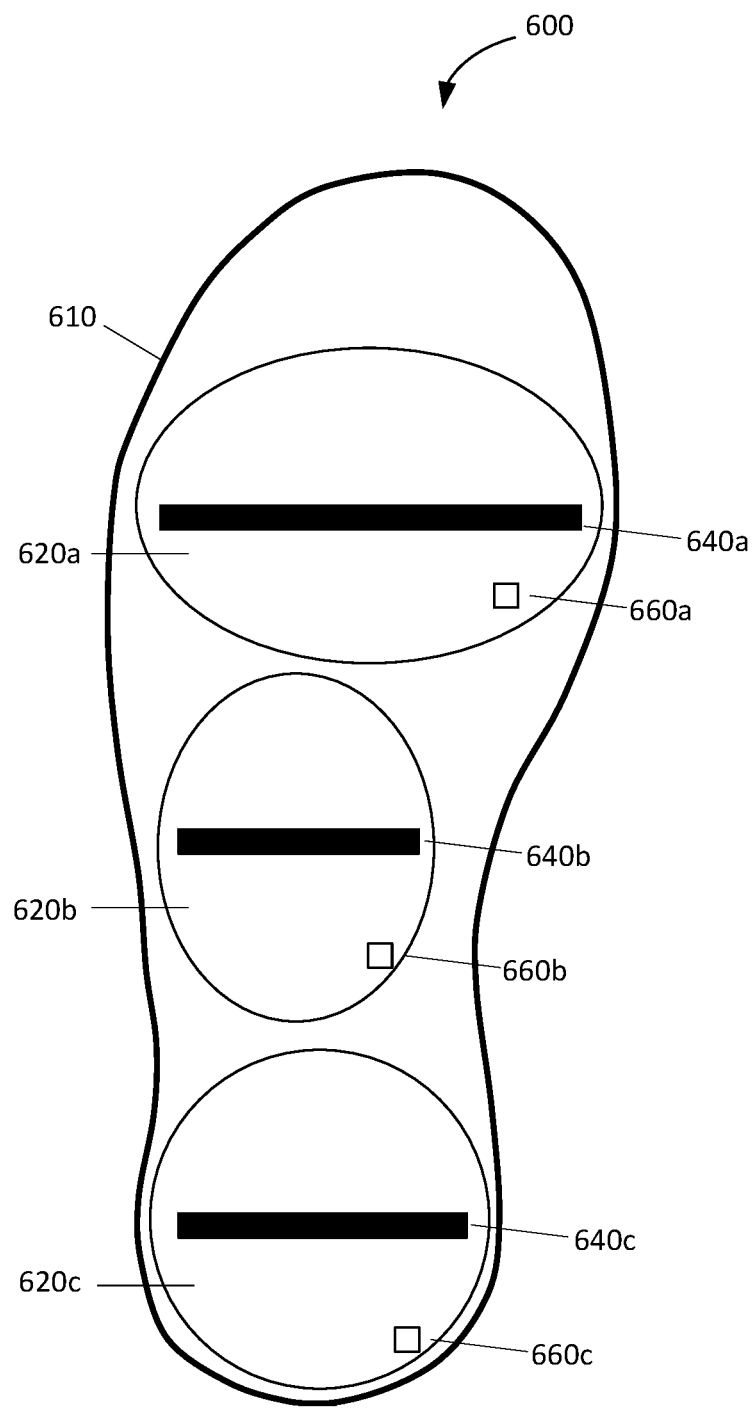
FIG. 7 is a top view of an insole for measuring the weight of a user according to an embodiment.

FIG. 7 is a top view of a device 600 for deformation measurement using multiple fluid reservoirs/bladders 620a, 620b, and 620c (sometimes collectively referred to herein as "bladders 620"). The bladders 620 can be positioned, for example, on the area of the insole 610 that corresponds to the ball of a user's foot 620a, the user's arch 620b, and the user's heel 620c. In some embodiments, more or fewer bladders 620 can be used. Using any number of bladders 620, various configurations can be deployed. In some embodiments, the bladders 620a-620c can be oriented differently with respect to the user's foot. In some embodiments, as illustrated in FIG. 7, there can be space between the bladders 620a-620c, and in other embodiments, the bladders 620 can closely border one another such that an edge of one bladder touches or nearly touches the edge of the next bladder. The bladders 620a-620c can therefore be various shapes and sizes.

At least one deformation sensor is used to determine the deformation and/or deformation change within the fluid reservoir 620. In some embodiments, there can be one deformation sensor disposed within, attached to, fluidically coupled to, placed in, or otherwise connected to each fluid reservoir. In some embodiments, the top and bottom substrates of each fluid reservoir 620 are made from the deformation sensor material. For example, as illustrated, deformation sensor 640a corresponds to fluid reservoir 620a, deformation sensor 640b corresponds to fluid reservoir 620b, and deformation sensor 640c corresponds to fluid reservoir 620c. In some embodiments, more than one deformation sensor can correspond with each fluid reservoir 620. When multiple deformation sensors 640a, 640b, and 640c (collectively referred to herein as "deformation sensors 540") are used, the multiple sensor measurements, or an indication thereof, can be synchronized and/or statistically analyzed in order to accurately determine the user's weight.

At least one communications component 660 (not shown) communicates the deformation and/or deformation change measurements, or an indication thereof, to a remote device (not shown). In some embodiments, the device 600 and/or the remote device is configured to determine the user's body weight based on the measurements. In some embodiments, a communications component 660 is provided for each of the sensors 640; for example, as illustrated in FIG. 7, the communications component 660a corresponds to deformation sensor 640a, the communications component 660b corresponds to deformation sensor 640b, and the communications component 660c corresponds to deformation sensor 640c. In some embodiments (not shown), one communications component 660 can correspond to more than one of the deformation sensors 640, and in some embodiments, one communications component 660 can correspond to all of the deformation sensors 640. The communications component 660 can be disposed within, attached to, fluidically coupled to, placed in, or otherwise connected to fluid reservoir 620, or can be disposed within, attached to, coupled to, placed in, placed on, or otherwise connected to the insole 610.

While the deformation sensors 640 and communications component 660 are shown in one orientation relative to the fluid reservoir 620, they can also be placed elsewhere relative to the fluid reservoir 620. A deformation sensor 640 can extend along the length and/or width of fluid reservoir 620. Multiple deformation sensors 640 can also be placed elsewhere along the fluid reservoir 620. In some embodiments, the deformation sensor 640 can be different shapes and sizes. For example, the deformation sensor 640 can be substantially circular, substantially square, substantially rectangular, or substantially triangular; it may be generally a polygon. The deformation sensor 640 can also be substantially linear. Furthermore, the deformation sensor 640 can extend the length and/or width of fluid reservoir 620, or can extend substantially the length and/or width of the fluid reservoir 620. For example, one deformation sensor 640 can extend substantially the length of the fluid reservoir 620a and another deformation sensor 640 can extend substantially the width of the fluid reservoir 620a.

Referring now to FIGS. 8A and 8B, the device 600 is illustrated in a first configuration and second configuration, respectively. In response to a force applied to the device in the direction of arrow B, the fluid reservoirs 620a-620c are compressed from the first configuration (FIG. 8A) to the second configuration (FIG. 8B). The force B can be, for example, the amount of force applied when the user steps on the insole 610. Each of the fluid reservoirs 620a-620c can deform when the force B is applied, thereby increasing the deformation within the fluid reservoirs 620a-620c, and this increased deformation and/or deformation change is measured by the corresponding sensors 640a-640c. The deformation measurements and/or deformation change measurements recorded by deformation sensors 640a-640c, or an indication thereof, can be communicated to a remote device (not shown) by the communications components 660a, 660b, and 660c and/or by a single communications component 660 (not shown). Due to the shape of the bottom of a user's foot, the force B applied to different parts of the insole 610 can vary. For example, the force applied by the heel of the user's foot can be higher than the force applied by the user's arch. Additionally, the fluid reservoirs 620a-620c can be made from different materials and filled with different fluids. Thus, the deformation and/or deformation change measurements recorded by the sensors 640a-640c can be different within each fluid reservoir 620a-620c. These measurements can therefore be synchronized and/or statistically analyzed to determine the weight of the user. The measurements can also be taken in a temporal format to obtain a time-dependent measurement of how the force propagates during a user's gait (for example, heel to arch to ball). This time-dependent information can be useful for analyzing gait, balance, and other such metrics.

Figure 9:
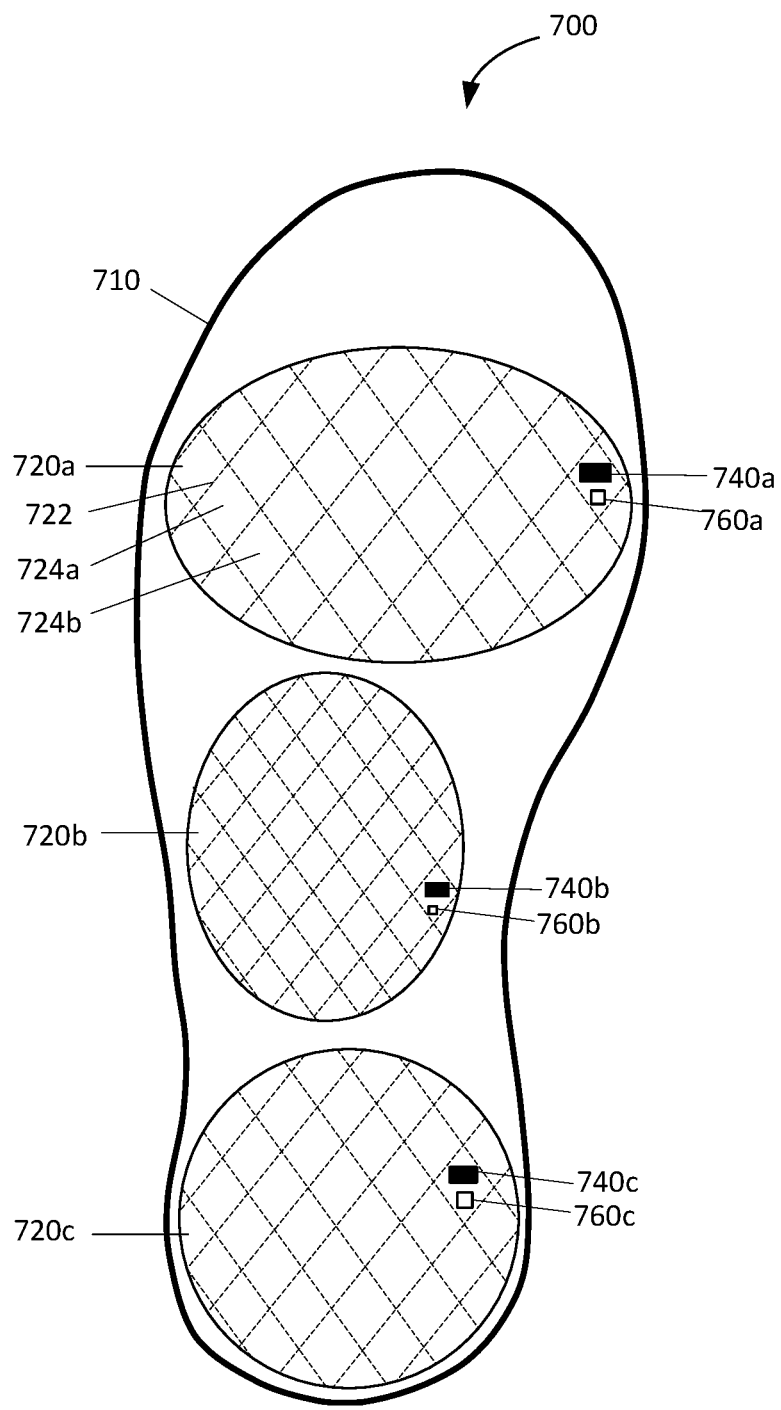
FIG. 9 is a top view of an insole for measuring the weight of a user according to an embodiment.

FIG. 9 is a top view of a device 700 for deformation measurement using multiple fluid reservoirs/bladders 720a, 720b, and 720c (sometimes collectively referred to herein as "bladders 720"). The bladders 720a-720c can be quilted so that the top and bottom substrate of the fluid reservoirs are connected in a pattern of relatively small, discrete intervals 722. The pattern of the intervals 722 can create portions/chambers 724a, and 724b (collectively referred to herein as "chambers 724"). Fluid can move between chambers, as it can flow in between the intervals 722 from the first chamber 724a to the second chamber 724b, and vice versa.

While fluid can flow between the chambers 724 within one of the fluid reservoirs, fluid cannot flow from one fluid bladder (e.g., bladder 720a) to another fluid bladder (e.g., bladder 720b). As illustrated in FIG. 9, each of the individual bladders 720a, 720b, and 720c are spaced apart from one another, but in other embodiments (not shown), the chambers can be adjacent to one another and/or separated by only a very small space. In some embodiments, the delineation between the bladders 720 can be along one or more of the patterned lines of intervals 722, where a continuous connection between the top and bottom substrate of the fluid reservoir is formed instead of the discrete intervals. This continuous connection between the top and bottom substrate of the fluid reservoir can provide a barrier through which the fluid within the bladders cannot pass, thus creating multiple bladders 720a-720c.

Deformation sensors 740a, 740b, and 740c (sometimes collectively referred to herein as "sensors 740") can measure the deformation and/or deformation changes within each of the bladders 720. These measurements can be synchronized and/or statistically analyzed to determine the weight of the user. The deformation and/or deformation changes, or an indication thereof, can be communicated to a user device (not shown) using communications components 760a, 760b, and 760c (collectively referred to herein as "communications components 760").

While the deformation sensors 740 and communications components 760 are shown in one orientation relative to the bladders 720 and chambers 724, they can also be placed elsewhere relative to the bladders 720 and chambers 724. Deformation sensors 740 can also extend along the length and/or width of multiple chambers 724. Multiple deformation sensors 740 can also be placed elsewhere along the bladders 720. For example, in some embodiments, one deformation sensor 740 can be oriented in each chamber 724, or deformation sensors 740 can be oriented in several chambers 724 within the bladders 720. In some embodiments, the deformation sensors 740 can be different shapes and sizes. For example, the deformation sensors 740 can be substantially circular, substantially square, substantially rectangular, or substantially triangular; it may be generally a polygon. The deformation sensors 740 can also be substantially linear. Furthermore, the deformation sensors 740 can extend the length and/or width of bladders 720, or can extend substantially the length and/or width of the bladders 720. For example, one deformation sensor 740 can extend substantially the length of the fluid reservoir 720a and another deformation sensor 740 can extend substantially the width of the fluid reservoir 720a. In these embodiments, the deformation sensor 740 extends across multiple chambers 724 in the fluid reservoir 720a.

Figure 10:
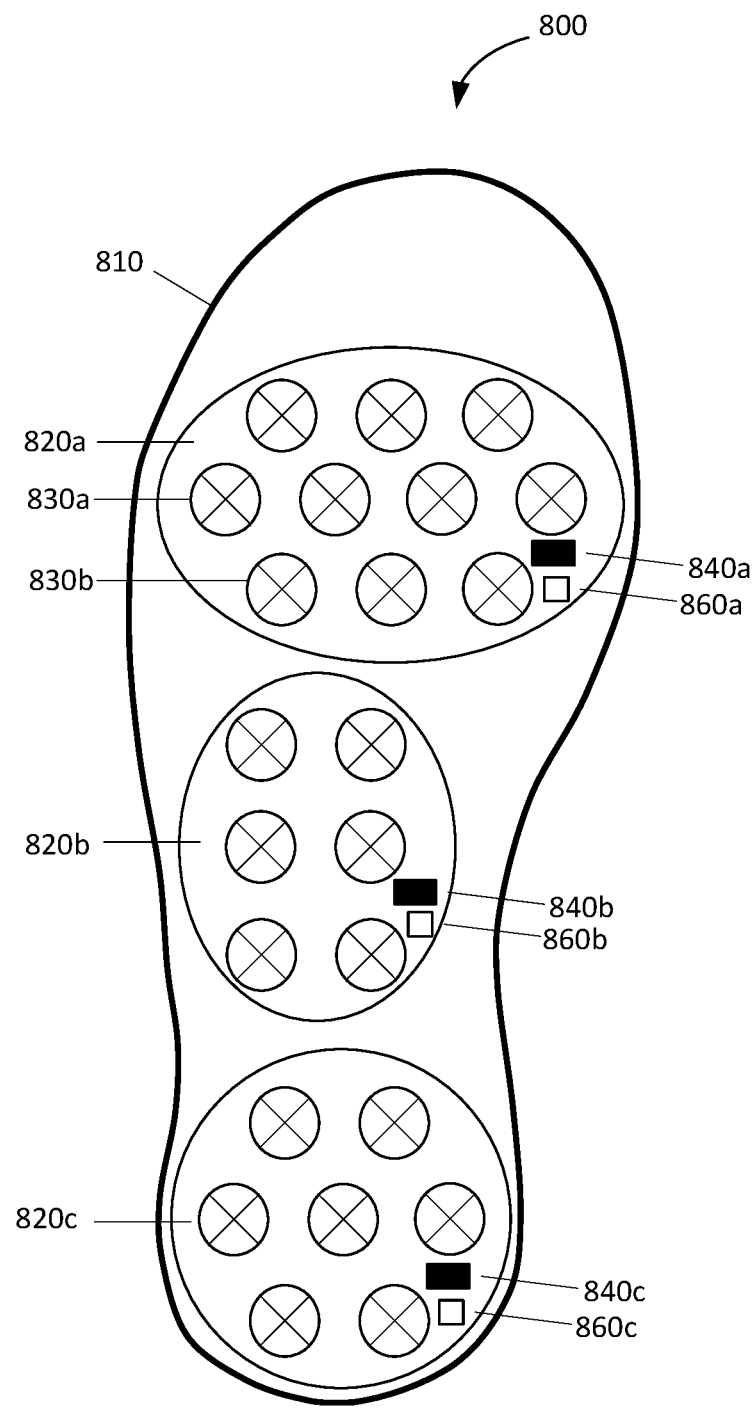
FIG. 10 is a top view of an insole for measuring the weight of a user according to an embodiment.

FIG. 10 is a top view of a device 800 for deformation measurement. The insole 810 can have multiple fluid reservoirs or bladders 820a, 820b, and 820c (sometimes collectively referred to herein as "bladders 820"). The top and bottom substrates of the bladders 820 can be connected to one another using supports 830a, and 830b (sometimes collectively referred to herein as "supports 830") arranged in a pattern. The supports 830 can be in predetermined locations within the bladders 820 and the fluid can pass freely around the supports 830 within each of the bladders 820. In some embodiments, the supports 830 can add structural support to the bladders 820. The supports 830 can be areas where the top and bottom substrates of the bladders 820 are connected without additional material between, or additional material can be used to provide additional structure. The deformation within each of the bladders 820 increases when the user steps on the insole 810, and the deformation sensors 840a, 840b, and 840c (collectively referred to herein as "sensors 840") can detect the deformation and/or deformation changes. Communications components 860a, 860b, and 860c (collectively referred to herein as "communications components 860") can transmit these measurements, or an indication thereof, to a remote device (not shown). In some embodiments, the device 800 and/or the remote device is configured to determine the user's body weight based on the measurements.

While the deformation sensors 840 and communications components 860 are shown in one orientation relative to the bladders 820 and supports 830, they can also be placed elsewhere relative to the bladders 820 and supports 830. Multiple deformation sensors 840 can also be placed elsewhere along the bladders 820. In some embodiments, the deformation sensors 840 can be different shapes and sizes. For example, the deformation sensors 840 can be substantially circular, substantially square, substantially rectangular, or substantially triangular; it may be generally a polygon. The deformation sensors 840 can also be substantially linear. Furthermore, the deformation sensors 840 can extend the length and/or width of bladders 820, or can extend substantially the length and/or width of the bladders 820. For example, one deformation sensor 840 can extend substantially the length of fluid reservoir 820a and another deformation sensor 840 can extend substantially the width of fluid reservoir 820a. In these embodiments, the deformation sensor 840 can extend across supports 830, as well as the top and/or bottom substrate of fluid reservoir 820a.

Although various embodiments have been described herein as having particular features and/or combinations of components, other embodiments are possible having a combination of any features and/or components of embodiments as discussed above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, .NET, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

The invention claimed is:

1. A device, comprising:
    an insole configured to be disposed under a foot of a user during use;
    a fluid reservoir formed at least partly within the insole, the fluid reservoir containing a fluid;
    a sensor configured to sense an indication of deformation associated with the fluid reservoir during use, the sensor extending along a longitudinal length of the insole from a first region of the insole disposable under a heel of the foot to a second region of the insole disposable under a toe of the foot;
    a communications component communicatively coupled to the sensor, the communications component configured to receive the indication of deformation from the sensor and to transmit deformation information associated with the indication of deformation to a remote device; and
    a processor configured to:
        determine a weight distribution of the user along the longitudinal length of the insole based on the indication of deformation;
        determine a transpose of the weight distribution along a direction extending along the longitudinal length of the insole; and
        determine a weight of the user by summing the transpose of the weight distribution.

2. The device of claim 1, the fluid reservoir including a plurality of portions, a first portion of the plurality of portions and a second portion of the plurality of portions in fluid communication with each other,
    the sensor configured to sense the indication of deformation associated with at least one of the first portion and the second portion.

3. The device of claim 1, the fluid reservoir including a plurality of portions, a first portion of the plurality of portions and a second portion of the plurality of portions being fluidically isolated from each other,
    the sensor configured to sense the indication of deformation associated with at least one of the first portion and the second portion.

4. The device of claim 1, the fluid reservoir including a plurality of portions, wherein the sensor is a first sensor fluidically coupled to a first portion of the plurality of portions, the first sensor configured to sense the indication of deformation associated with the first portion,
    the device further comprising a second sensor fluidically coupled to a second portion of the plurality of portions of the fluid reservoir, the second sensor configured to sense an indication of deformation associated with the second portion.

5. The device of claim 1, the fluid including one or more of a gas, liquid, foam, gel, and combinations thereof.

6. The device of claim 1, the fluid reservoir including a valve configured for one or more of:
    filling the fluid reservoir with the fluid; and
    draining the fluid from the fluid reservoir.

7. The device of claim 1, the fluid reservoir including a plurality of portions, a first portion of the plurality of portions made from a first material and a second portion of the plurality of portions made from a second material, the first material being different from the second material in thickness.

8. The device of claim 1, the fluid reservoir including a plurality of portions, wherein a first portion of the plurality of portions at least partly overlays a second portion of the plurality of portions during use.

9. The device of claim 1, the fluid reservoir including a plurality of portions, at least one portion of the plurality of portions formed under at least one of:
    a ball of the foot of the user during use;
    an arch of the foot of the user during use; and
    the heel of the foot of the user during use.

10. The device of claim 1, at least a portion of the fluid reservoir formed under a ball of the foot of the user during use.

11. The device of claim 1, at least a portion of the fluid reservoir formed under an arch of the foot of the user during use.

12. The device of claim 1, at least a portion of the fluid reservoir formed under the heel of the foot of the user during use.

13. The device of claim 1, wherein the indication of deformation includes an indication of one or more of absolute deformation and absolute deformation change.

14. The device of claim 1, the sensor further configured to sense a temperature of the fluid reservoir or in proximity thereof, or to sense a temperature of the insole or in the proximity thereof, or both.

15. The device of claim 1, wherein the sensor is a first sensor, further comprising a second sensor configured to sense a temperature of the fluid reservoir or in proximity thereof, to sense a temperature of the insole or in the proximity thereof, or both.

16. The device of claim 1, wherein the sensor is a first sensor and the indication of deformation is a first indication of deformation,
further including one or more additional sensors configured to sense additional indications of deformation in the fluid reservoir during use.

17. The device of claim 1, further comprising:
a memory configured to store the indication of deformation,
the memory further configured to store the weight of the user,
the communication component configured to transmit the weight of the user to the remote device.

18. The device of claim 1, the sensor including one or more of a stretch sensor, a distributed strain sensor, a force sensor, a strain gauge, a piezoresistor, a semiconductor gauge, and combinations thereof.

19. The device of claim 1, the fluid reservoir formed using a top substrate and a bottom substrate, the top substrate and the bottom substrate coupled to one another via a plurality of supports, the plurality of supports configured to provide structural support to the insole and the fluid reservoir.

20. The device of claim 1, the sensor configured to sense the indication of deformation along a plurality of axes.

21. The device of claim 1, the fluid reservoir formed using a top substrate and a bottom substrate, the top substrate and the bottom substrate coupled to one another according to a pattern of discrete points to provide a plurality of chambers in which the fluid contained within a chamber can flow into an adjacent chamber.

22. A method, comprising:
sensing, via a sensor extending along a longitudinal length of an insole from a first region of the insole disposable under a heel of a foot to a second region of the insole disposable under a toe of the foot, an indication of deformation in a fluid reservoir formed at least partly within the insole when the insole is disposed under a foot of a user, the fluid reservoir containing a fluid;
transmitting, via a communications component communicatively coupled to the sensor and that receives the indication of deformation from the sensor, deformation information associated with the indication of deformation to a remote device;
determining, via a processor, a weight distribution of the user along the longitudinal length of the insole based on the indication of deformation;
determining, via the processor, a transpose of the weight distribution along a direction extending along the longitudinal length of the insole; and
determining, via the processor, a weight of the user by summing the transpose of the weight distribution.

23. The method of claim 22, the fluid reservoir including a plurality of portions, a first portion of the plurality of portions and a second portion of the plurality of portions in fluid communication with each other,
the sensing including sensing the indication of deformation in at least one of the first portion and the second portion.

24. The method of claim 22, the fluid reservoir including a plurality of portions, a first portion of the plurality of portions and a second portion of the plurality of portions being fluidically isolated from each other,
the sensing including sensing the indication of deformation in at least one of the first portion and the second portion.

25. The method of claim 22, further comprising sensing a temperature of the fluid reservoir or in the proximity thereof, or sensing a temperature of the insole or in the proximity thereof, or both.

26. A kit, comprising:
a first device, the first device being wearable by a user and including a first communications component; and
a second device, including:
an insole configured to be disposed under a foot of the user during use;
a fluid reservoir formed at least partly within the insole, the fluid reservoir containing a fluid;
a sensor configured to sense an indication of deformation associated with the fluid reservoir during use, the sensor extending along a longitudinal length of the insole from a first region of the insole disposable under a heel of the foot to a second region of the insole disposable under a toe of the foot;
a second communications component communicatively coupled to the sensor, the second communications component configured to receive the indication of deformation from the sensor and to transmit deformation information associated with the indication of deformation to the first communications component of the first device; and
a processor configured to:
determine a weight distribution of the user along the longitudinal length of the insole based on the indication of deformation;
determine a transpose of the weight distribution along a direction extending along the longitudinal length of the insole; and
determine a weight of the user by summing the transpose of the weight distribution.

\* \* \* \* \*